(12) United States Patent
Saifullah et al.

(10) Patent No.: US 8,389,501 B2
(45) Date of Patent: Mar. 5, 2013

(54) ANTICANCER COMPOUND

(76) Inventors: Saifullah, Karachi (PK); Saifullah Khan, Karachi (PK); Azizuddin, Karachi (PK); Muhammad Kashif, Karachi (PK); Ahsana Dar, Karachi (PK); Muhammad Iqbal Choudhary, Karachi (PK)

(*) Notice: Subject to any disclaimer, the term of this patent is extended or adjusted under 35 U.S.C. 154(b) by 0 days.

(21) Appl. No.: 13/184,548

(22) Filed: Jul. 17, 2011

(65) Prior Publication Data

US 2013/0018025 A1    Jan. 17, 2013

(51) Int. Cl.
*A61K 31/60* (2006.01)
*A61K 31/59* (2006.01)

(52) U.S. Cl. ........................ 514/167; 514/160
(58) Field of Classification Search .............. 514/160, 514/167
See application file for complete search history.

(56) References Cited

U.S. PATENT DOCUMENTS

2002/0077291 A1* 6/2002 Upshall et al. .................. 514/12
2008/0138379 A1* 6/2008 Jennings-Spring ........... 424/423

OTHER PUBLICATIONS

Scifinder appendage of compound (2003).*
Cos et al., "Structure-Activity Relationship and Classification of Flavonoids as Inhibitors of Xanthine Oxidase and Superoxide Scavengers," J. Nat. Prod., 61: 71-76 (1998).
SciFinder—CAS Registry No. 65-04-3, Extracted Oct. 15, 2012.

* cited by examiner

*Primary Examiner* — Shirley V Gembeh
(74) *Attorney, Agent, or Firm* — Sarfaraz K. Niazi

(57) ABSTRACT

*Azadirachta indica* cell suspension culture is used to metabolize dianabol to yield potent anticarcinogenic 17β-hydroxy-17α-methyl-5α-androst-1-en-3-one, which can also be synthesized.

3 Claims, 3 Drawing Sheets

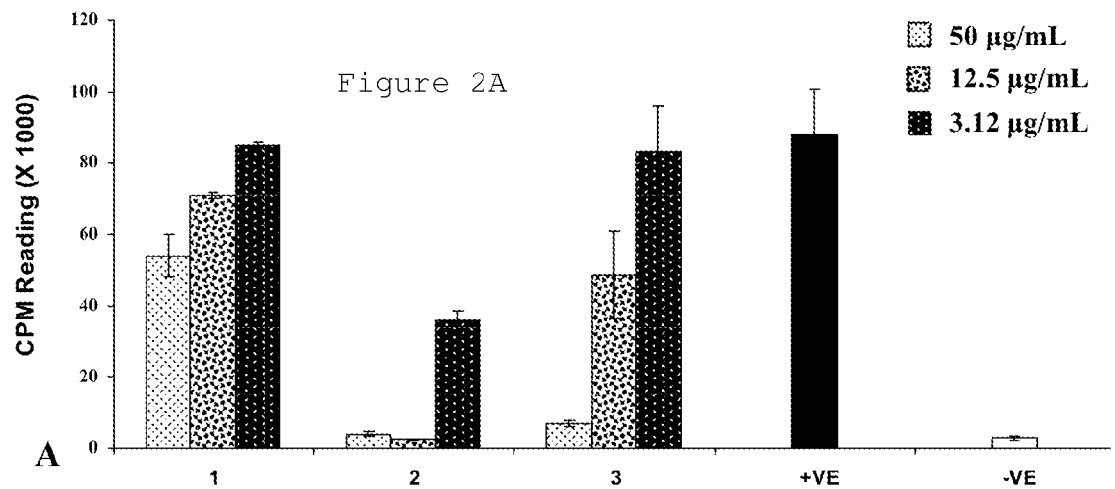
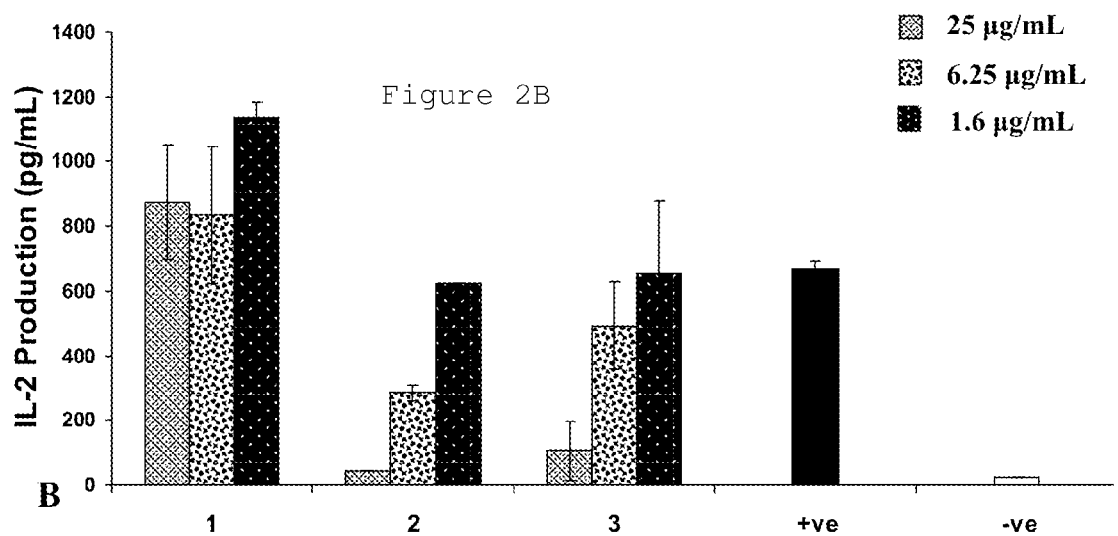

ANTICANCER COMPOUND

BACKGROUND

*Azadirachta indica* cell suspension culture can be used for the biotransformation of dianabol (Compound 1) to yield metabolites including 17β-hydroxy-17α-methyl-5α-androst-1-en-3-one (Compound 2), and 17β-hydroxy-17α-methyl-5α-androstan-3-one (Compound 3); these can be alternately synthesized chemically. The structures of these compounds were deduced on the basis of various spectroscopic techniques.

Compound 2 exhibited a significant immunomodulatory inhibitory activity and strongly suppressed the PHA-activated T-cell proliferation ($IC_{50}$: <10.33 µM) comparable to control drug prednisolone, after 72 hours incubation, and was further found to interfere with the IL-2 production ($IC_{50}$: 16.89±1.32) (FIG. 2A). Compound 2 also exhibited anticancer activity against lung cancer cell line; NCI-H460, it moderately inhibited the growth of cancer cells (22.5±4.15 µM).

Compound 3 exerted a moderate inhibitory activity on both tests as compared to Compound 2. On the other hand, the Compound 1 did not show any significant effect on the tested system.

Molecular docking studies were also performed to speculate possible interaction among IL-2 protein, and biotransformed products; studies exhibited a good correlation between the predicted binding energies of the compounds acquired by the FlexX program and the experimental affinities. For docking studies, crystal structure of human IL-2 complexed with Compound 4 [(R)—N-[2-[1-(aminoiminomethyl)-3-piperidinyl]-1-oxoethyl]-4-(phenylethynyl)-L-phenylalanine methyl ester] was downloaded from Protein data bank (pdb id: 1M48).

SUMMARY OF THE INVENTION

Plant cell suspension cultures can serve as tools for the in vivo production of secondary metabolites (1,2), as well as for the biotransformation of xenobiotics (3-5). These cultures are considered to be useful biocatalysts for reactions, such as hydroxylation at allylic positions, oxidation-reduction between alcohols and ketones, and the reduction of carbon-carbon double bonds (6,7). Plant cell culture-mediated biotransformations are now increasingly employed by synthetic chemists for the structural modifications of various organic compounds in addition to using standard synthetic techniques.

Plant enzyme biocatalysts may be applied to the production of totally new drugs and also may be used to modify existing drugs by improving their bioactivity spectrum. The introduction of a functional group into terpenoids, and steroids is an important reaction in synthetic chemistry. Many studies have been reported on the specific oxidation, reduction of olefins, and alicyclic hydrocarbons with chemical reagents (8-10). The ability of cultured plant cells to transform organic compounds is useful for mass production of substances; however, chemical synthesis of these compounds remains a possibility. Plant cell cultures and microbacteria are considered to be useful biocatalysts for reactions such as the hydroxylation at allylic positions, the oxidation-reduction of alcohols and ketones, and reduction of carbon-carbon double bonds (11).

In the instant invention, biotransformation of Compound 1 was obtained by incubating it with *Azadirachta indica* cell suspension cultures (12-13). This yielded Compounds 2 and 3, resulting from the sequential reduction of olefinic double bonds. The structures of transformed compounds were deduced by various spectroscopic methods.

DETAILED DESCRIPTION OF THE INVENTION

Compound 1, a potent steroid, is a derivative of testosterone, exhibiting strong anabolic and moderate androgenic properties. This Compound was first made available in 1960, and it quickly became the most favoured and widely used anabolic steroid by athletics.

Human health is directly influenced by the immune systems, and their performance, which are fundamentally designed for the protection against the attack of foreign invaders. However the onset of almost all infectious and degenerative diseases is largely due to inadequate or hyperactive immune response. Therefore, the modulation of the immune system is highly relevant to the control of numerous immunological disorders.

The instant invention reports the immunomodulatory actions of Compound 2, which is found capable of reducing the PHA dependant Th1 response induced in human peripheral mononuclear cells.

The molecular characteristics of Compounds 1-3, possibly associated with the inhibition of IL-2 protein, were also performed using modelling study involving the FlexX program to dock the compounds 1-3, along with the reference inhibitor Compound 4, into the active site of the IL-2 protein.

Usually docking protocol is evaluated through re-docking process in which the co-crystallized Compound is extracted and re-docked into the binding cavity, and the quality of docking protocol is evaluated through root mean square deviation (RMSD≦2 Å is considered as best). In this invention, Compound 4 was used as a reference for docking studies. Compound 4 synthesis has been reported by Tiley et al (27) and its chemical characterization is reported. The Compound was co-crystallized with IL-2 by Arkin et al (28). The re-docking of Compound 4, suggested that the docking protocol is suitable for the docking analysis of newly identified IL-2 inhibitors (Compounds 1-3).

BRIEF DESCRIPTION OF DRAWINGS

FIG. 2: Effect of Compounds 1-3 on phytohemagglutinin (PHA) T-cell proliferation and production. (2A) The bar graph represents effects of various concentrations of the test Compounds 1-3 after 72 h incubation with peripheral blood mononuclear cells at 37° C. Effect of compounds on T-cell proliferation response is compared with non-proliferated (+ve) and proliferated (−ve) cells. The bar graph (2B) represents effects of various concentrations of the test Compounds 1-3 on production of IL-2 compared with (+ve) and without (−ve) PHA induced IL-2 production. Each bar represents the mean value of triplicate reading±SD.

BIOTRANSFORMATION STUDIES

Figure 1:
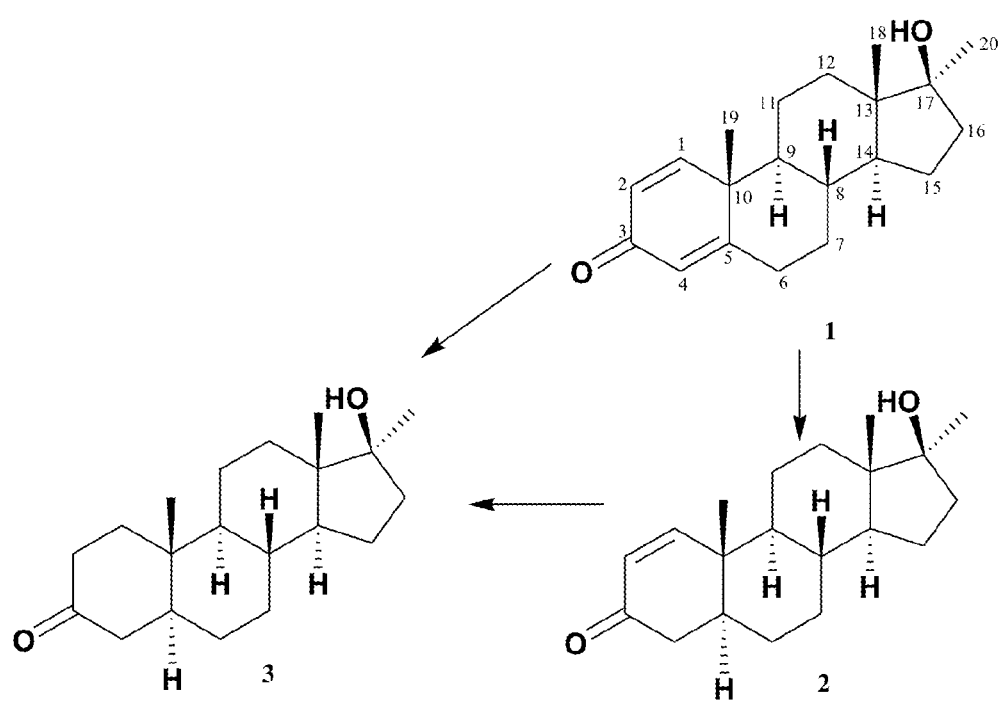
FIG. 1: Biotransformation of dianabol (Compound 1) by cell suspension cultures of *Azadirachta indica*, and resulting metabolites, Compounds 2 and 3.
Figure 3:
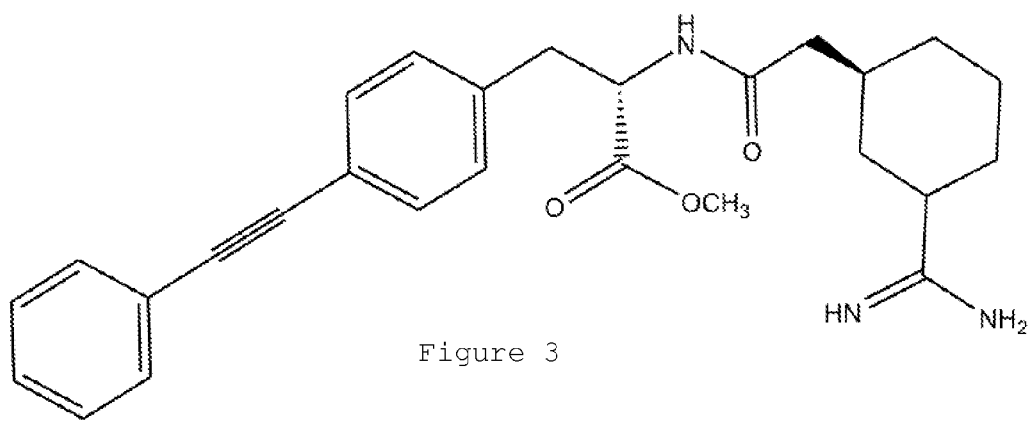
FIG. 3: Chemical structure of Compound 4.

Biotransformation of Compound 1 by cell suspension culture of *Azadirachta indica* A Juss, yielded compounds 2 and 3, (FIG. 1).

FIG. 1

Compound 2 was obtained as a colorless solid. The molecular formula $C_{20}H_{30}O_2$ was deduced from the HREI-MS at m/z 302.0122 (Calculated at 302.0120), indicating six degrees of unsaturation. The IR spectrum showed hydroxyl absorption at 3445, and carbonyl absorption at 1674 cm$^{-1}$. The $^1$H NMR spectrum of Compound 2 displayed only one olefinic double bond at $\delta_H$ 7.13, and 5.83 (each d, $J_{1,2}$=10.2 Hz) (Table-1).

TABLE 1

$^1$H NMR (300 MHz, CDCl$_3$)$^a$) chemical shifts of Compound 1 and its metabolites 2 and 3. $\delta$ in ppm and J in Hz.

| Compound NO | 1 | 2 | 3 |
|---|---|---|---|
| 1 | 7.03 (d, $J_{1,2}$ = 10.2) | 7.13 (d, $J_{1,2}$ = 10.2) | 2.05 – 2.08 (m)$^b$ |
| 2 | 6.19 (dd, $J_{2,1}$ = 10.2, | 5.83 (d, $J_{2,1}$ = 10.2) | 1.68 – 1.70 (m) |
| 3 | — | — | — |
| 4 | 6.04 (br. s) | 2.20 – 2.23 (m) | 2.06 – 2.08 (m)$^b$ |
| 5 | — | 1.92 – 1.94 (m) | 1.93 – 1.95 (m) |
| 6 | 2.32 – 2.34 (m) | 2.28 – 2.30 (m) | 2.30 – 2.32 (m) |
| 7 | 1.28 – 1.30 (m) | 1.32 – 1.35 (m) | 1.30 – 1.32 (m) |
| 8β | 1.67 – 1.70 (m)$^c$ | 1.50 – 1.52 (m) | 1.47 – 1.50 (m) |
| 9α | 1.00 – 1.02 (m) | 1.15 – 1.18 (m) | 0.92 – 0.95 (m) |
| 10 | — | — | — |
| 11 | 1.62 – 1.64 (m)$^b$ | 1.63 – 1.65 (m)$^b$ | 1.51 – 1.53 (m) |
| 12 | 1.20 – 1.22 (m) | 1.21 – 1.23 (m) | 1.18 – 1.20 (m)$^c$ |
| 13 | — | — | — |
| 14α | 1.15 – 1.18 (m) | 1.12 – 1.14 (m) | 1.18 – 1.20 (m)$^c$ |
| 15 | 1.30 – 1.32 (m) | 1.41 – 1.44 (m)$^c$ | 1.36 – 1.38 (m) |
| 16 | 1.68 – 1.70 (m)$^c$ | 1.71 – 1.73 (m) | 1.64 – 1.66 (m) |
| 17 | — | — | — |
| 18 | 0.91 (s) | 0.87 (s) | 0.85 (s) |
| 19 | 1.22 (s) | 1.01 (s) | 1.01 (s) |
| 20 | 1.16 (s) | 1.20 (s) | 1.19 (s) |

$^a$assignments based on COSY and HMQC;
$^{b,c}$signals may be interchanged.

The $^{13}$C NMR spectra also showed disappearance of one olefinic double bond in the Compound 2. It showed additional signal of C-4 methylene ($\delta_C$ 41.0), and C-5 methene ($\delta_C$ 44.4) (Table-2). This reduction also confirmed by the HMBC spectrum, in which C-1 ($\delta_H$ 7.13) have $J_2$ correlations with C-2 ($\delta_C$ 127.5), and C-10 ($\delta_C$ 39.1), and $J_3$ correlations with C-3 ($\delta_C$ 200.1) and C-5 ($\delta_C$ 44.4). Similarly, C-5 ($\delta_H$ 1.92-1.94, m) showed $J_2$ correlations with C-4 ($\delta_C$ 41.0), and C-10 ($\delta_C$ 39.1), and $J_3$ correlation with C-3 ($\delta_C$ 200.1). The configuration of the newly introduced proton at C-5 was assigned to be α on the basis of NOESY correlation between H-5 with CH$_3$-20α, which showed a trans junction between rings A and B. Thus, the structure of Compound 2 was identified as 17β-hydroxy-17α-methyl-5α-androst-1-en-3-one (14).

Compound 3 was also obtained as a white solid. The HREI-MS of Compound 3 showed the M$^+$ at m/z 304.2113, corresponding to the formula C$_{20}$H$_{32}$O$_2$ (Calculated at 304.2115). The IR spectrum showed a hydroxyl absorption at 3360, and ketonic absorption at 1713 cm$^{-1}$. The reduction of both olefinic double bonds was inferred by the absence of the all downfield olefinic protons in the $^1$H NMR spectrum of Compound 3 (Table-1). The $^{13}$C NMR spectra of Compound 3 also showed three additional upfield methylene and a methine carbon signals i.e. C-1 ($\delta_C$ 38.2), C-2 (39.0), C-4 (44.7) and C-5 ($\delta_C$ 46.8), (Table-2). In the HMBC spectrum, C-19 methyl protons ($\delta_H$ 1.01) showed $J_2$ correlations with C-10 ($\delta_C$ 35.8), and $J_3$ correlations with C-1 ($\delta_C$ 38.2), and C-5 ($\delta_C$ 46.8). The configuration of the newly introduced proton at C-5 was assigned to be a on the basis of NOESY correlation between H-5 with CH$_3$-20α, which supported a trans junction between rings A and B.[15] The complete $^1$H and $^{13}$C NMR assignments of Compound 3 are presented in Tables-1 and -2, respectively.

TABLE 2

$^{13}$C NMR (100 MHz, CDCl$_3$)$^a$)$^b$) chemical shifts of Compound 1 and its metabolites 2 and 3.

| C. NO. | 1 | 2 | 3 |
|---|---|---|---|
| 1 | 155.7(d) | 158.3(d) | 38.2 (t) |
| 2 | 127.5(d) | 127.5(d) | 39.0 (t) |
| 3 | 186.2(s) | 200.1(s) | 211.9(s) |
| 4 | 123.8(d) | 41.0 (t) | 44.7 (t) |
| 5 | 169.0(s) | 44.4(d) | 46.8(d) |
| 6 | 32.8 (t) | 27.6 (t) | 28.9 (t) |
| 7 | 33.3 (t) | 31.6 (t) | 31.6 (t) |
| 8 | 36.4(d) | 36.6(d) | 36.2(d) |
| 9 | 52.5(d) | 50.7(d) | 53.9(d) |
| 10 | 43.6(s) | 39.1(s) | 35.8(s) |
| 11 | 22.5 (t) | 20.9 (t) | 21.1 (t) |
| 12 | 31.3 (t) | 31.0 (t) | 31.5 (t) |
| 13 | 45.6(s) | 45.7(s) | 45.6(s) |
| 14 | 49.8(d) | 50.1(d) | 50.6(d) |
| 15 | 23.3 (t) | 23.2 (t) | 23.3 (t) |
| 16 | 38.7 (t) | 39.0 (t) | 38.6 (t) |
| 17 | 81.3(s) | 81.5(s) | 81.6(s) |
| 18 | 13.9(q) | 14.1(q) | 14.0(q) |
| 19 | 18.7(q) | 13.1(q) | 11.5(q) |
| 20 | 25.8(a) | 25.9(a) | 25.8(a) |

$^a$)multiplicities were determined by DEPT experiments;
$^b$)assignment based on HMQC and HMBC.

Biological Studies

Anti-Inflammatory:

In this invention, effects of Compounds 2 and 3 on the innate immune response, in particular the reactive oxygen species (ROS) production was examined using whole blood phagocytes, and isolated neutrophils, which did not result in any significant effect (Table 3). In addition to that, effects of these compounds on T-cells proliferation were also evaluated; investigating their (Compounds 2 and 3) ability to modulate PHA activated T-cell proliferation response and production of IL-2 cytokine.

Compound 2 was found to have significant inhibitory activity on T-cell proliferation with IC$_{50}$ value less than 10.33 µM compared to Compound 1, which did not show any significant effect neither on T-cells proliferation nor IL-2 production. A moderate inhibitory activity with IC$_{50}$ value of 42.11 µM was obtained with Compound 3. The activity of these Compounds 2 and 3 was further confirmed by their effects on IL-2 cytokine production, which is the main contributor in T-cell activation. The extracellular production of IL-2 from peripheral blood mononuclear cells was significantly inhibited (IC$_{50}$=16.9±1.32 µM) by Compound 2. On the other hand, Compound 3 was having a moderate inhibitory effect (IC$_{50}$=49.3±1.32 µM) on IL-2 production (FIG. 2B). The activity of Compound 2, in contrast to the 1 and 3, could be due to the olefinic bond between C-1/C-2. Compound 3 did not possess a carbon-carbon double bond, and showed lesser activity (Table-3). This suggested the activity might be due to C-1/C-2 carbon-carbon double bond.

TABLE 3

Comparative $IC_{50}$ effect of Compound 1 and its transformed metabolites, Compounds 2 and 3 on oxidative burst of whole blood, isolated polymorphoneutrophils (PMNs), T-cell proliferation and IL-2 cytokine

| Comp. Code | Oxidative burst $IC_{50}$ (μM) on Whole blood | Oxidative burst $IC_{50}$ (μM) on PMNs | T-Cell proliferation $IC_{50}$ (μM) | IL-2 $IC_{50}$ (μM) |
|---|---|---|---|---|
| 1 | >333.33 | >166.67 | >166.67 | >166.67 |
| 2 | >331.13 | >165.56 | <10.33 | 16.89 ± 1.32 |
| 3 | >328.95 | >164.47 | 42.11 ± 11.51 | 49.34 ± 1.32 |

Anti-Cancerous:

Compounds 1-3 were also screened for the anticancer activity against NCI-H460 cell line. Compound 2 gave the best results having $GI_{50}$ value 22.5±4.15 μM which means, at this concentration this Compound inhibited 50% growth of the respective cell line i.e., NCI-H460 (Table 4). Comparing the $GI_{50}$ values of Compounds 1 and 3, this is the lowest effective concentration of the three compounds used against NCI-H460. Compounds 1-3 have similar structures (FIG. 1) except for one and two oleifinic double bonds. Compound 2 differs by absence of one and 3 by two oleifinic double bonds. Interestingly, Compound 2 has a difference of only one oleifinic double bonds at C-4 position as compared to its parent compound; probably due to the absence of this double bond Compound 3 was not able to inhibit considerable growth of cancer cells at 100 μM that is why this Compound was not evaluated further. And Compound 1 (substrate), which is different having two oleifinic double bond (at C-1 and C-4 positions) exhibited better growth inhibition but not as discriminating as Compound 2, which clearly suggested that absence and presence of oleifinic double bond in the given structures, is important for having the anticancer activity. Particularly, double bond present at position C-4 is more important than at C-1. Consequently Compounds 1 and 2 showed anticancer activity but Compound 3 was non-active against NCI-H460 cell line.

TABLE 4

Growth inhibition induced by transformed compounds against human lung cancer cell line (NCI-H460).

| Compound(s)* | $GI_{50}$ (μM) | TGI (μM) |
|---|---|---|
| doxorubicin (control) | 0.08 ± 0.02 | — |
| 1 | 28.3 ± 2.72 | ND |
| 2 | 22.5 ± 4.15 | 60 ± 9.2 |
| 3 | ND | ND |

ND: Values could not be determined indicates <50% inhibition of cell growth at maximum dose (100 μM) tested.

Docking Studies

Docking studies showed a good correlation between the predicted binding energies of the compounds obtained by the FlexX program, and the experimental binding affinities (Table-5).

TABLE 5

Docking Energies and H-Bond Distances with the Arg38.

| Compounds | Binding Scores | H-bond Distance (Å) |
|---|---|---|
| | | Arg38 |
| 4 | −26.0 | |
| 3 | −9.8 | 3.207 (NH2η$^1$) |

TABLE 5-continued

Docking Energies and H-Bond Distances with the Arg38.

| Compounds | Binding Scores | H-bond Distance (Å) |
|---|---|---|
| 2 | −10.8 | 1.820 (NH2η$^1$) and 2.962 (NH2η$^2$) |
| 1 | −6.7 | — |

Analysis of the docking results revealed that all three compounds bind at the same receptor site on the surface of IL-2 protein. Comparing the binding scores of the Compounds 1-3, with that of the reference ligand, it was predicted that Compounds 1-3 could inhibit IL-2 protein. All three compounds showed similar binding pattern and interacts on the active site of IL-2 protein at the surface through several active-site amino acid residues.

Compound 1 was the least active due to the presence of two olefinic double bonds in conjugation with the carbonyl group of ring A at C-3. The lone pair of the carbonyl group is least likely to be available to interact with surrounding amino acid residues due to conjugation. While in Compound 2, the carbonyl group of ring A interact with NH2η$^1$ of Arg38 with a weak hydrogen bond (3.207 Å), which is due to the most suitable geometry of ring A.

Olefinic double bond at C-1 is the difference between Compounds 2 and 3, and Compound 3 lacks any olefinic double bond. This structural difference makes the Compound 2 most active. The carbonyl group of ring A at C-3 position interact with the side chain amino groups of Arg38, and create two hydrogen bonds at a distance of 1.8 and 1.9 Å with NH2η$^1$ and NH2η$^2$ of Arg38, respectively. All three compounds are additionally stabilized by a number of hydrophobic interactions with the active site amino acids, notably Lys35, Arg38, Met39, Thr41, Phe42, Lys43, Phe44, Pro65, Val69, Leu72, and Ala73 at the A'B loop of the IL-2.

The docking results revealed the importance of Arg38 in the vicinity of carbonyl group of ring A, which plays a vital role in protein-ligand complex formation and stabilization.

Experimental

General Methods

The $^1$H-NMR spectra were recorded in CDCl$_3$ on Bruker AM-300 and AM-400 NMR spectrometers with TMS as an internal standard using UNIX operating system at 300 and 400 MHz, respectively. The $^{13}$C-NMR spectra were recorded in CDCl$_3$ at 100 MHz on Bruker AM-400 NMR spectrometer. HREI-MS were recorded on Jeol JMS 600 and HX 110 mass spectrometers with the data system DA 5000. The IR spectra were recorded on a Jasco A-302 spectrophotometer. The UV spectra were recorded on a Hitachi U-3200 spectrophotometer. The optical rotations were measured on JASCO DIP-360 digital polarimeter. The melting point was determined on a Buchi 510 apparatus. Column chromatography (CC) was carried on silica gel column (70-230 Mesh). Purity of the samples was checked by TLC on pre-coated silica gel GF-254 preparative plates (20×20 cm, 0.25 mm thick, Merck) and were detected under the UV lights (254 and 366 nm), while ceric sulphate was used as spraying reagent. Dianabol (Compound 1) was purchased from Fluka Riedel-deHaën®.

Callus Culture

The callus cultures of the plant were derived from young leaves cultivated in 300 mL jars, each having 25 mL of Murashige and Skoog media (16), supplemented with sucrose (30 g/L), 3-indole butyric acid (IBA) (19.7 μM), and 6-benzyl aminopurine (BA) (4.44 μM), and solidified by agar (6 g/L) at 25±1° C. under complete darkness.

Biotransformation Protocol

Cell suspension cultures were derived from static cultured cells in Erlenmeyer flasks (1,000 mL), each containing 400 mL of the Murashige and Skoog media, supplemented with ingredients as mentioned above, except BA and agar. After 15 days of pre-culturing on a gyratory platform shaker at 100 rpm, and with a 16 h photoperiod at 25±1° C., a solution of substrate (100 mg in 1 mL of acetone) was added to each flask through a 0.2 μM membrane filter, and the flasks were placed on a shaker for 20 days. Taking aliquots from culture on daily basis carried out the time course study and TLC was used to analyse the content of transformation. A negative control containing only plant cell suspension cultures, and a positive control-containing Compound 1 in the media were also prepared in order to check the presence of plant metabolites in the cell culture, and the chemical changes as a result of chemical reaction (if any) due to media components, respectively.

Extraction and Isolation Procedure

After 20 days of incubation, the cells and the media were separated by filtration. The filtrate was extracted with $CH_2Cl_2$ (3×1.5 L) and the cells were extracted in an ultrasonic bath with $CH_2Cl_2$ (3×500 mL) at room temperature. The combined extract were dried over anhydrous $Na_2SO_4$, and concentrated under reduced pressures, which afforded a brown residue (1.32 g). The transformed metabolites were isolated from this gummy crude by using repeated column chromatography (silica gel) with petroleum ether/EtOAc gradient, afforded metabolites 2 (26 mg, petroleum ether:EtOAc, 9.5:0.5, 5.2% yield) and 3 (18 mg, petroleum ether:EtOAc, 9.8:0.2, 3.6% yield).

17β-Hydroxy-17α-methyl-5α-androst-1-en-3-one (Compound 2)

Colorless solid, m.p. 140-142° C., $[\alpha]D^{20}$ −40° (c 0.04, $CHCl_3$). UV (MeOH) $\lambda_{max}$ (log ε): 230 nm (3.62). IR ($CHCl_3$) $\nu_{max}$: 3445 (OH), 1674 (C=O), 1652, 1496 (C=C), 1380 $cm^{-1}$ (C—O). EI-MS m/z (rel. int. %): 302 (10), 284 (3), 245 (15), 232 (3), 200 (5), 160 (18). HREI-MS m/z: 302.0122 ($M^+$, $C_{20}H_{30}O_2$; calcd 302.0120). $^1H$ ($CDCl_3$, 300 MHz) and $^{13}C$ NMR ($CDCl_3$, 100 MHz) data listed in Tables-1 and -2, respectively.

17β-hydroxy-17α-methyl-5α-androstan-3-one (Compound 3)

Colorless solid, m.p. 152-154° C., $[\alpha]D^{20}$ −130° (c 0.02, $CHCl_3$). UV (MeOH) $\lambda_{max}$ (log ε): 203 nm (0.43). IR ($CHCl_3$) $\nu_{max}$: 3360 (OH), 1713 (C=O), 1372 $cm^{-1}$ (C—O). EI-MS m/z (rel. int. %): 304 (20), 289 (28), 271 (15), 247 (45), 231 (39), 215 (14), 189 (12), 175 (16), 163 (46). HREI-MS m/z: 304.2113 ($M^+$, $C_{20}H_{32}O_2$; calcd 304.2115). $^1H$ ($CDCl_3$, 300 MHz), and $^{13}C$ NMR ($CDCl_3$, 100 MHz) data listed in Tables-1 and -2, respectively.

[(R)—N-[2-[1-(Aminoiminomethyl)-3-piperidinyl]-1-oxoethyl]-4-(phenylethynyl)-L-phenylalanine methyl ester](Compound 4)

Immunomodulatory Studies

Reagents, Chemicals, and Equipment

Luminol (3-aminophthalhydrazide), Hanks Balance Salts Solution (HBSS) and Lymphocytes Separation Medium (LSM) were purchased from Research Organics, Sigma, Germany, and MP Biomedicals, Inc., Germany, respectively. Zymosan-A (*Saccharomyces cerevisiae* origin), Dimethylsulfoxide (DMSO), ethanol and ammonium chloride of analytical grades were purchased from Merck Chemicals, Darmstadt, Germany. The luminometer used was Luminoskan RS, Finland.

Isolation of Human Polymorphonuclear Cells (PMNs)

Heparinized blood was obtained by vein puncture aseptically from healthy volunteers (25-38 years age). The buffy coat containing PMNs was collected by dextran sedimentation and the cells were isolated after the LSM density gradient centrifugation from the tube base. Cells were washed twice and suspended in Hank's Balance Salt Solution ($Ca^{2+}$ and $Mg^{2+}$ free) ($HBSS^{--}$), pH 7.4. Neutrophils were purified from RBCs contamination using hypotonic solution. Cells were adjusted to their required concentration using Hank's Balance Salt Solution containing $Ca^{2+}$ and $Mg^{2+}$ ($HBSS^{++}$).

Oxidative Burst Study

Luminol-enhanced chemiluminescence assay was performed as described by Helfand et al. (17), and Haklar et al. (18) with some modifications. Briefly, 25 μL diluted whole blood (1:200 dilution in sterile $HBSS^{++}$) or 25 μL of PMNs (1×10$^6$) cells were incubated with 25 μL of serially diluted compounds with concentration ranges between 3.2-50 mg/mL. Tests were performed in white 96-well plates, which were incubated at 37° C. for minutes in the thermostated chamber of the luminometer. Opsonized zymosan-A, 25 μL, followed by 25 μL luminol (7×10$^{-5}$ M) along with $HBSS^{++}$ was added to each well to obtain a 100 μL volume/well. Wells received $HBSS^{++}$, and cells but no compounds were used as a negative control. Chemiluminescence peaks were recorded with the Luminometer. Results were monitored as chemiluminescence relative light units (RLU) with peak and total integral values.

T-Cell Proliferation Assay

The T-cell proliferation assay was performed as described by Nielson et al. (19). In this assay, isolated lymphocytes were stimulated by adding the phytohemagglutinin (PHA) in culture. The rate of proliferation and survival was measured by radiolabelled thymidine incorporation method. The lymphocytes were isolated as described by Boyum (20). A 50 μL of cell suspension (10$^6$/mL) was added to each well of a 96-well round bottom tissue culture plate. 50 μL of PHA was added in each well from the working solution (20 μg/mL) to have final concentration 5 μg/mL. The final volume was adjusted to 200 μL in each well by adding complete RPMI media. The plates were incubated at 37° C. for 72 hours (90% humidity, 5% $CO_2$/air). Methyl-$^3H$ thymidine (Amersham Pharmacia Biotech) 0.5 μCi was added in each well and incubated for further 18 hours. Cells were harvested on a filter mat (Type G-7) using cell harvester (INOTECH IH-280, Switzerland) and the radioactivity (CPM) was measured using a β-scintillation counter (LS 6500, Beckman Coulter, USA). (FIG. 2A) FIG. 2

IL-2 Cytokine Production

IL-2 cytokine was produce from peripheral blood mononuclear cells (PBMC). IL-2 cytokine production by PHA activated cells in the presence or absence of test compounds was studied by ELISA using the human cytokine kit (Diaclone, Besancon Cedex France). Briefly, freshly prepared mononuclear cells (10$^5$/well) were cultured in 96-well microtiter flat bottom plate in the presence or absence of 5 μg/mL PHA. Four different concentrations (10.33-331.13 μM/mL) of compounds, along with PHA, were used in this assay. The culture plate was incubated at 37° C. for 18 h. Then the supernatant was collected and analyzed for IL-2 cytokine production following kit manufacturer instructions.

Statistical Analysis

Students T-test was performed to compare the significance mean differences between the control and tested extracts for various chemiluminescence results. The differences were considered to be significant at levels of $P \leq 0.05$.

Anticancer Activity

The sulforhodamine B (SRB) protein-staining assay was employed for measurement of in vitro growth inhibition and cytotoxicity (21) The appropriate cell density (cells/well) of NCI-H460 cells ($1 \times 10^4$) was added in 96-well plates. The cell density used was dependent on the doubling time of the cell line leading to the formation of monolayer. After 24 h incubation, different doses of Compounds 1-3 were added and incubated for further 48 h. This was followed by fixation of cells with ice-cold trichloroacetic acid (50 µl, 50%) at room temperature for 30 min. The plates were carefully washed five times with distilled water, and left for overnight drying in air. Sulforhodamine B dye (100 µl, 0.4% in 1% acetic acid) was introduced in each well and after 30 min residual dye was removed using acetic acid (1%) and air-dried overnight. The bound SRB dye was solubilized in Tris-base solution (100 µl, 10 mM) with gentle shaking on a plate-shaker for 5 min prior to optical density (OD) measurements at 545 nm in a plate reader. Drug concentrations causing growth inhibition ($GI_{50}$) of 50% cells were calculated from dose response curves and total growth inhibition of Compound 2 was also evaluated.

Molecular Docking Protocol

The protein data bank file, PDB id; 1M48 (2.0 Å structure resolution) of the Human Interleukin-2 complexed with Compound 4 was obtained from the protein data bank [Research Collaboratory for Structural Bioinformatics (RCSB) (http://www.rcsb.org/pdb)]. The three-dimensional structures of compounds 1-3 were generated by molecular modelling software SYBYL 6.9.[22] Energy minimization was carried out using the Tripos force field with a distance gradient algorithm with a convergence criterion of 0.05 kCal/(molÅ), and maximum 10,000 iterations, respectively, with Gasteiger-Hückel charges (23).

Docking of Compounds 1-3 into the active site of IL-2 receptor was performed using FlexX docking software implemented in SYBYL6.9 (23). FlexX software is a fast and flexible algorithm for docking small ligand into binding sites of the enzymes, using an incremental construction algorithm that actually builds the ligand in the binding site (24). The software incorporates protein-ligand interactions, placement of the ligand core, and rebuilding of the complete ligand. A receptor description file (RDF) was created from the PDB coordinates. The active site for docking was defined as all atoms within 6.5-Å radius of the co-crystallized Compound 4. The proposed interaction mode of the ligand in the active-site of IL-2 was determined as the highest scored conformation (best fit ligand) among 30-generated conformations and binding modes generated according to FlexX scoring function, which is the structure with the most favorable free energy of binding. Docking results were analyzed by VMD (visual molecular dynamics) (25).

REFERENCE

1. Charlwood, B. V.; Rhodes, M. J. C. *Secondary Products from Plant Tissue Cultures*; Clarendon Press: Oxford, 1990; pp 167-200
2. Lowe, K. C.; Davey, M. R.; Power, J. B. Plant tissue culture: past, present and future. *Plant Tiss. Cult. Biotechnol.* 1996, 2, 175-186.
3. Reihard, E.; Alfermann, Fiechter, A. W. *Advances in Biochemical Engineering*; Springer: New York, 1980; pp. 49-83
4. Charlwood, B. V.; Hegarty, P. K.; Charlwood, K. A.; Lippin, G.; Tampion, J.; Stride J. In *Secondary Metabolism in Plant Cell Cultures*. Morris, P.; Scragg, A. H.; Stafford, A.; Fowler, M. W., Eds.; Cambridge University Press: London, 1986; pp 113-116.
5. Dia, J.; Guo, H.; Lu, D.; Zhu, W.; Zhang, D.; Zheng J.; Guo, D. Biotransformation of 2α, 5α, 10α, 14α, tetra acetoxy-(20), 11 taxadiene by ginkgo cell suspension cultures. *Tettrahedron Lett.* 2001, 42, 4677-4679.
6. Suga, T.; Hirata, T. Biotransformation of exogenous substrates by plant cell cultures. *Phytochemistry*, 1990, 29, 2393-2406.
7. Ishihara, K.; Hamada, H.; Hirata, H.; Nakajima N. Biotransformation using plant cultured cells. *J. Mol. Catal. B: Enzym.* 2003, 23, 145-170.
8. Mukaiyama, T.; Yamada, T.; Nagata, T.; Imagawa, K. Asymmetric Aerobic Epoxidation of Unfunctionalized Olefins Catalyzed by Optically Active α-Alkoxycarbonyl-β-ketoiminato Manganese (III) Complexes. *Chem. Lett.* 1993, 2, 327-330.
9. Sharpless, K. B.; Amberg, W.; Bennani, Y. L.; Crispino, G. A.; Hartung, J.; Jeong, K.; Kwong H.; Morikawa, K.; Wang, Z.; Xu, D.; Zhang, X. The osmium-catalyzed asymmetric dihydroxylation: a new ligand class and a process improvement. *J. Org. Chem.* 1992, 57, 2768-2771.
10. Sakamaki, H.; Take, M.; Matsumoto, T.; Iwadare, T.; Ichinohe, Y. Transformation of cycloartanyl acetate into B-homo triterpenoids. *J. Org. Chem.* 1988, 53, 2622-2624.
11. Sakamakia, H.; Itoha, K. I.; Taniaib, T.; Kitanakac, S.; Takagid, Y.; Chaie, W. Horiuchie, C. A. *J. Mol. Cat. B: Enzym.* 2005, 32, 103-106.
12. Choudhary, M. I.; Siddiqui, Z. A.; Khan, S., Saifullah; Musharraf, S. G.; Atta-ur-Rahman. Biotransformation of (−)-Caryophyllene Oxide by Cell Suspension Culture of *Catharanthus roseus. Z. Naturforsch*, 2006, 61b, 197-200.
13. Azizuddin; Saifullah; Khan, S.; Choudhary, M. I.; Atta-Ur-Rahman. Biotransformation of Dydrogesterone by Cell Suspension Cultures of *Azadirachta indica. Turk. J. Chem.* 2008, 32, 141-146.
14. Hampel, V. B.; Kraemer, J. M. Die Kernresonanzspektren Von Steroiden In Polaren Lösungsmitten II. *Tetrahedron*, 1966, 22, 1601-1613
15. Thevis M.; Schänzer W. Mass Spectrometric Analysis of Androstan-17β-ol-3-one and androstandiene-17β-ol-3-one isomers. *J. Am. Chem. Soc. for mass spectrum.* 2005, 16, 1660-1669.
16. Murashige, T.; Skoog, F. A revised medium for rapid growth and biossays with tobacco tissue cultures. *Physiol. Plant.* 1962, 15, 473-497.
17. Helfand, S.; Werkmeister, J.; Roder, J. Chemiluminescence response of human natural killer cells. The relationship between target cell binding, chemiluminescence, and cytolysis. *J. Exp. Med.* 1982, 156, 492-505.
18. Haklar, G.; Ozveri, E. S.; Yuksel, M.; Aktan, A.; Yalynn, A. S. Different kinds of reactive oxygen and nitrogen species were detected in colon and breast tumors. *Cancer Lett.* 2001, 165, 219-224.
19. Nielsen, M.; Gerwien, J.; Nielsen, M.; Geisler. C.; Ropke, C.; Svejgaard, A.; Odum, N. MHC class II ligation induces CD58 (LFA-3)-mediated adhesion in human T cells. *Exp. Clin. Immunogenet.* 1998, 15, 61-68.
20. Boyum, A. Isolation of mononuclear cells and granulocytes from human blood. Isolation of mononuclear cells by one configuration, and of granulocytes by combining centrifugation and sedimentation. *Scand. J. Clin. Lab. Invest.* 1968, 21, 77-89.
21. Skehan, P.; Streng, R.; Scudiero, D.; Monks, A.; McMahon, J.; Vistica, D.; Warren, J. T.; Bokesch, H.; Kenney, S.; Boyd, M. R. New colorimetric cytotoxicity assay for anticancer drug screening. *J. Natl. Cancer Inst.,* 1990, 82, 1107-1112.
22. SYBYL molecular modeling software. Tripos Associated Ltd., St. Louis Mo.
23. TRIPOS Inc., 1699 South Hanley Road, St. Louis, Mo. 63144, USA
24. Rarey, M.; Kramer, B.; Lengauer, T.; Klebe, G. A fast flexible docking method using an incremental construction algorithm. *J. Mol. Biol.* 1996, 261, 470-489.
25. Visual Molecular Dynamics Version 1.8.6, Theoretical and computational Biophysics Group, University of Illinois & Beckman Institute, 405 N. Matthews, Urbana, Ill. 61801.
26. Jefferson W. Tilley, Li Chen, David C. Fry, S. Donald Emerson, Gordon D. Powers, Denise Biondi, Tracey Varnell, Richard Trilles, Robert Guthrie, Francis Mennona, Gerry Kaplan, Ronald A. LeMahieu, Mathew Carson, Ru-Jen Han, C.-M. Liu, Robert Palermo, and Grace Ju, Identification of a Small Molecule Inhibitor of the IL-2/IL-2Rr Receptor Interaction Which Binds to IL-2 *J. Am. Chem. Soc.* 1997, 119, 7589-7590.
27. Michelle R. Arkin, Mike Randal, Warren L. DeLano, Jennifer Hyde, Tinh N. Luong, Johan D. Oslob, Darren R. Raphael, Lisa Taylor, Jun Wang, Robert S. McDowell, James A. Wells, and Andrew C. Braisted, Binding of small molecules to an adaptive protein-protein interface, PNAS, 2003, 100, 1603-1608.

What we claim is:

1. A method of treating lung cancer comprising administering a therapeutically effective amount of 17β-hydroxy-17 (α-methyl-5α-androst-1-en-3-one.

2. The method of claim 1 wherein the mode of treatment includes administering a dosage form containing sufficient quantity of 17β-hydroxy-17α-methyl-5α-androst-1-en-3-one and pharmaceutical adjuvants.

3. The method of claim 1 wherein 17β-hydroxy-17α-methyl-5α-androst-1-en-3-one is obtained as a biotransformation product of dianabol contacted with a suspension of Azadirachata indica cell culture under suitable conditions.

* * * * *